(12) United States Patent
Hruschka et al.

(10) Patent No.: US 10,813,815 B2
(45) Date of Patent: Oct. 27, 2020

(54) TILTABLE PATIENT-SUPPORTING APPARATUS AND METHOD OF TILTING A PATIENT-SUPPORTING APPARATUS

(71) Applicants: Klaus Hruschka, Erbendorf (DE); Richard Kellner, Pullenreuth (DE); Philip Materne, Kulmain (DE); Patrick Plannerer, Erbendorf (DE)

(72) Inventors: Klaus Hruschka, Erbendorf (DE); Richard Kellner, Pullenreuth (DE); Philip Materne, Kulmain (DE); Patrick Plannerer, Erbendorf (DE)

(73) Assignee: Siemens Healthcare GmbH, Erlangen (DE)

( * ) Notice: Subject to any disclaimer, the term of this patent is extended or adjusted under 35 U.S.C. 154(b) by 211 days.

(21) Appl. No.: 15/411,948

(22) Filed: Jan. 20, 2017

(65) Prior Publication Data

US 2017/0128303 A1 May 11, 2017

Related U.S. Application Data

(62) Division of application No. 14/711,261, filed on May 13, 2015.

(30) Foreign Application Priority Data

May 13, 2014 (DE) .................. 10 2014 209 016

(51) Int. Cl.
*A61G 13/04* (2006.01)
*A61G 7/005* (2006.01)
(Continued)

(52) U.S. Cl.
CPC .............. *A61G 13/04* (2013.01); *A61B 6/04* (2013.01); *A61B 6/0457* (2013.01); *A61G 7/005* (2013.01);
(Continued)

(58) Field of Classification Search
CPC ........ A61G 13/04; A61G 13/06; A61G 7/005; A61G 7/012; A61G 7/018; A61G 2200/32;
(Continued)

(56) References Cited

U.S. PATENT DOCUMENTS 682,932 A 9/1901 Haltom
3,623,617 A 11/1971 Nemessanyi
(Continued)

FOREIGN PATENT DOCUMENTS

CN 101150988 A 3/2008
CN 101166500 A 4/2008
(Continued)

OTHER PUBLICATIONS

German Office action for related German Application No. 10 2014 209 016.4, dated Feb. 3, 2015, with English Translation.
(Continued)

*Primary Examiner* — Eric J Kurilla
*Assistant Examiner* — Amanda L Bailey
(74) *Attorney, Agent, or Firm* — Lempia Summerfield Katz LLC

(57) ABSTRACT

A patient-supporting apparatus includes a lifting apparatus. The lifting apparatus includes an upper part, a lower part, and a lifting linkage. The lifting linkage connects the upper part to the lower part and has at least one scissors-form sub-linkage having a central articulation. A point of rotation of the central articulation is arranged in a displaceable manner such that the upper part may be tilted in a transverse direction.

11 Claims, 4 Drawing Sheets

(51) Int. Cl.
*A61G 7/012* (2006.01)
*A61G 13/06* (2006.01)
*A61B 6/04* (2006.01)
*A61G 7/018* (2006.01)

(52) U.S. Cl.
CPC .............. *A61G 7/012* (2013.01); *A61G 7/018* (2013.01); *A61G 13/06* (2013.01); *A61G 2200/32* (2013.01); *A61G 2210/50* (2013.01)

(58) Field of Classification Search
CPC .... A61G 2210/50; A61B 6/04; A61B 6/0457; B66F 7/0666; B66F 7/0675; B66F 7/0683; B66F 7/065; B66F 7/22
See application file for complete search history.

(56) References Cited

U.S. PATENT DOCUMENTS

| | | | |
|---|---|---|---|
| 3,624,782 A * | 11/1971 | McPeek | B65G 57/035 |
| | | | 414/793.4 |
| 3,902,616 A | 9/1975 | Santic et al. | |
| 4,078,269 A | 3/1978 | Weipert | |
| 4,684,314 A | 8/1987 | Luth | |
| 5,074,000 A | 12/1991 | Soltani et al. | |
| 5,676,424 A * | 10/1997 | Winkelhake | B60N 2/1803 |
| | | | 248/421 |
| 6,416,219 B1 | 7/2002 | Pflaum et al. | |
| 6,726,279 B1 | 4/2004 | Figel et al. | |
| 6,974,123 B2 * | 12/2005 | Latvys | B66F 7/065 |
| | | | 254/122 |
| 9,463,966 B1 | 10/2016 | Damabi | |
| 2006/0026762 A1 | 2/2006 | Hornbach et al. | |
| 2007/0079443 A1 | 4/2007 | Hoth et al. | |
| 2007/0221895 A1 | 9/2007 | Pieger et al. | |
| 2008/0190707 A1 | 8/2008 | Hoth | |
| 2009/0038073 A1 | 2/2009 | Dippl et al. | |
| 2009/0049613 A1 | 2/2009 | Dippl et al. | |
| 2009/0300844 A1 | 12/2009 | Taylor | |
| 2016/0060084 A1 * | 3/2016 | Baudermann | B66F 7/0625 |
| | | | 414/347 |

FOREIGN PATENT DOCUMENTS

| | | |
|---|---|---|
| CN | 101244007 A | 8/2008 |
| CN | 202568726 U | 12/2012 |
| CN | 202594718 U | 12/2012 |
| DE | 1804765 A | 1/1960 |
| DE | 3519820 A1 | 12/1986 |
| DE | 4238733 A1 | 5/1994 |
| DE | 20216647 * | 1/2003 |
| DE | 19920008 B4 | 4/2004 |
| DE | 102004016728 A1 | 10/2005 |
| EP | 1732840 B1 | 4/2011 |

OTHER PUBLICATIONS

Chinese Office Action for related Chinese Application No. 2015 101 937 82.X dated May 27, 2017, with English Translation.

* cited by examiner

TILTABLE PATIENT-SUPPORTING APPARATUS AND METHOD OF TILTING A PATIENT-SUPPORTING APPARATUS

This application is a divisional patent application of U.S. patent application Ser. No. 14/711,261, filed on May 13, 2015, which claims the benefit of DE 10 2014 209 016.4, filed on May 13, 2014. These patent documents are hereby incorporated by reference in their entirety.

FIELD

The present embodiments relate to a tiltable patient-supporting apparatus with a lifting apparatus and a method of tilting such a patient-supporting apparatus.

BACKGROUND

Patient-supporting apparatuses may be adjusted vertically in height by a lifting apparatus. DE 10 2004 016 728 A1 discloses a lifting apparatus having an upper part and a lower part. The lifting apparatus has a lifting linkage that connects the upper part to the lower part and has two sub-linkages that are connected to one another via connecting articulations. The lifting apparatus also has a drive unit for adjusting the height of the upper part. The drive unit acts on one of the connecting articulations.

FIG. 1 shows an oblique view of such a lifting apparatus 1. The lifting apparatus 1 includes a lower part 2, in the form of a base plate, an upper part 3, for accommodating a patient support, and a lifting linkage 4 that is configured in the form of a double scissors mechanism or double scissors structure. The lifting apparatus includes two scissors-structure pairs 5, 6 as sub-linkages. The two scissors-structure pairs 5, 6 are connected to one another in an articulated manner.

The lower scissors-structure pair 6 is connected to the base plate 2 in an articulated manner via front scissors feet 7. Rear scissors feet 8 of the lower scissors-structure pair 6 are connected to one another via a slide that, when the double scissors structure 4 is opened and closed, runs back and forth in the running direction 11 on a running rail (not visible) fastened on the base plate 2.

Between the front and the rear scissors feet 7, 8 of the lower scissors-structure pair 6, a horizontally arranged electric motor 12 is fastened on the base plate 2. The axis of rotation 13 of the electric motor 12 runs parallel to the running direction 11 of the slide 9 (not visible). There is sufficient space for arranging a measure-control (not depicted) above the electric motor 12.

Located between the front scissors feet 7 is a toothed gear mechanism 14 that converts the rotary movement of the electric motor 12 into a linear movement of a telescopic spindle 15. The telescopic spindle runs perpendicularly to the axis of rotation 13 of the electric motor 12 and is arranged between the front scissors-structure feet 7 and beneath the front connecting articulation 16 of the double scissors structure 4. The telescopic spindle 15 is configured in the form of a trapezoidal screw spindle and has a spindle head connected in an articulated manner to the front connecting articulation 16 of the double scissors structure 4 via a transverse connection 17.

For a height adjustment of the upper part 3, the electric motor 12 is switched on, and the telescopic spindle 15 is extended and/or retracted. The connecting articulation 16 of the double scissors structure 4 executes a rectilinear movement in the vertical direction 18 at a constant speed. The slide moves in the running direction 11. The axis of rotation 13 of the electric motor 12 runs perpendicularly to the spindle axis.

In radiography, for a fair number of imaging-recording operations and interventions, for a patient lying on a patient-supporting apparatus, the patient is to be tilted about a horizontal transverse axis (e.g., transverse to the direction in which the patient is lying). This allows internal organs to be displaced or moved into a position that is advantageous for image-recording purposes (e.g., for recording images of the abdomen or thorax).

SUMMARY AND DESCRIPTION

The scope of the present invention is defined solely by the appended claims and is not affected to any degree by the statements within this summary.

The present embodiments may obviate one or more of the drawbacks or limitations in the related art. For example, a tiltable patient-supporting apparatus and a method for tilting a patient-supporting apparatus are provided.

According to one or more of the present embodiments, a tilting movement of the patient-supporting apparatus is generated via a displacement of the point of rotation in the central articulation of a scissors-form lifting linkage. The displacement may take place either in a purely translatory manner via a linear guide or in rotary manner via an eccentric.

One or more of the present embodiments provide a patient-supporting apparatus with a lifting apparatus. The lifting apparatus includes an upper part, a lower part, and a lifting linkage that connects the upper part to the lower part. The lifting linkage includes at least one scissors-form sub-linkage having a central articulation. The point of rotation of the central articulation is configured to be moveable (e.g., in a translatory or rotary manner), and therefore, the upper part may be tilted in the transverse direction (e.g., about a transverse axis of a patient).

It is an advantage of the present embodiments that, without any additional subassemblies being provided between a lifting scissors structure and a table top (e.g., upper part) or between the lower part and the lifting scissors structure, a tilting movement may be generated. The necessary amount of installation space thus remains small, and the minimum rise height may be kept as low as possible.

A further advantage is that many of the components used in known lifting scissors structures may be used without modification (e.g., linear guide at the bottom, lifting drive, lifting linkage at the bottom, table top/lifting scissors structure interface, etc.), and the tilting mechanism may be integrated in existing lifting scissors structures e.g., retro-fitting).

In a development of the apparatus, the upper part may be configured in the form of a table top or for a table top to be arranged on the upper part.

In a further embodiment, the patient-supporting apparatus includes two sub-linkages that are arranged one above the other and are connected to connecting articulations so as to form a double scissors structure. The central articulation may be formed in the upper sub-linkage or in both sub-linkages.

In a further embodiment, the patient-supporting apparatus includes a first scissors arm and a second scissors arm that form the sub-linkage and are connected to one another by the central articulation such that the first scissors arm and the second scissors arm may be rotated about the point of rotation. The apparatus also includes a slot that is formed in the first scissors arm and in which the point of rotation of the central articulation is arranged in a displaceable manner. A linear guide is formed in this way.

In a further configuration, the patient-supporting apparatus includes a first drive unit that displaces the point of rotation in the slot.

In a further embodiment, the patient-supporting apparatus includes a first scissors arm and a second scissors arm that form the sub-linkage and are connected to one another by the central articulation such that the first scissors arm and the second scissors arm may be rotated about the point of rotation. The central articulation is configured in the form of an eccentric that rotates the point of rotation eccentrically. A rotating movement may thereby be provided.

In a development, the apparatus includes a second drive unit that rotates the eccentric.

In one embodiment, the apparatus includes a third drive unit, for adjusting the height of the upper part. The third drive unit acts on one of the connecting articulations.

In one embodiment, the third drive unit may be configured for a rectilinear movement of the upper part in the vertical direction.

One or more of the present embodiments also provide a method of tilting a patient-supporting apparatus. The point of rotation of the central articulation is moved such that the upper part is tilted in the transverse direction (e.g., about a transverse axis formed transversely to the direction in which a patient is supported).

DETAILED DESCRIPTION

Figure 2A:
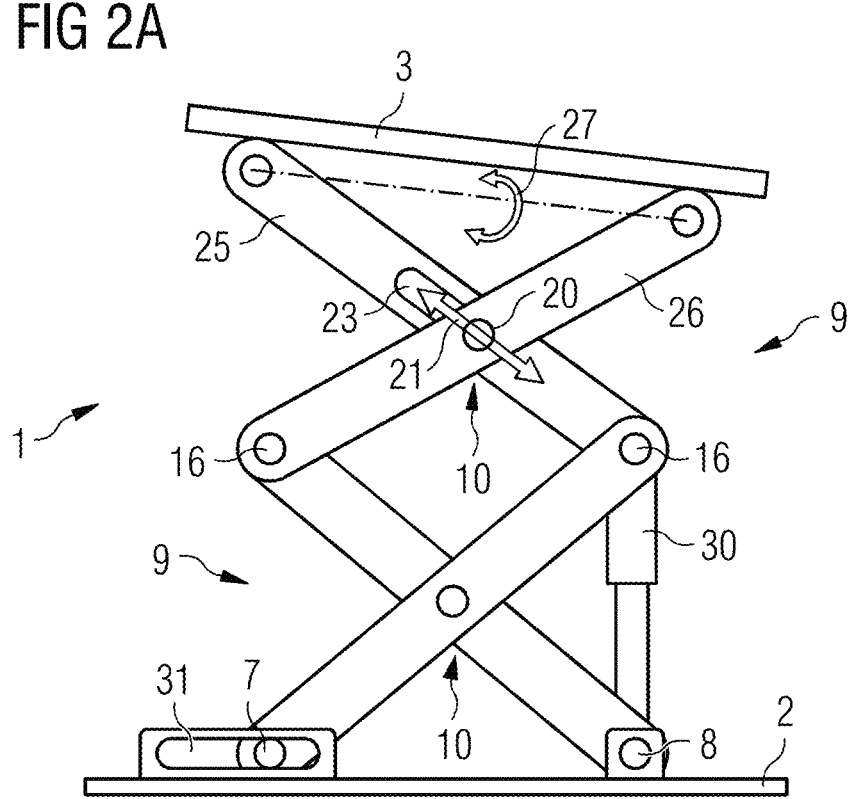
FIGS. 2A-2C shows three side views of one embodiment of a tiltable patient-supporting apparatus.
Figure 2B:
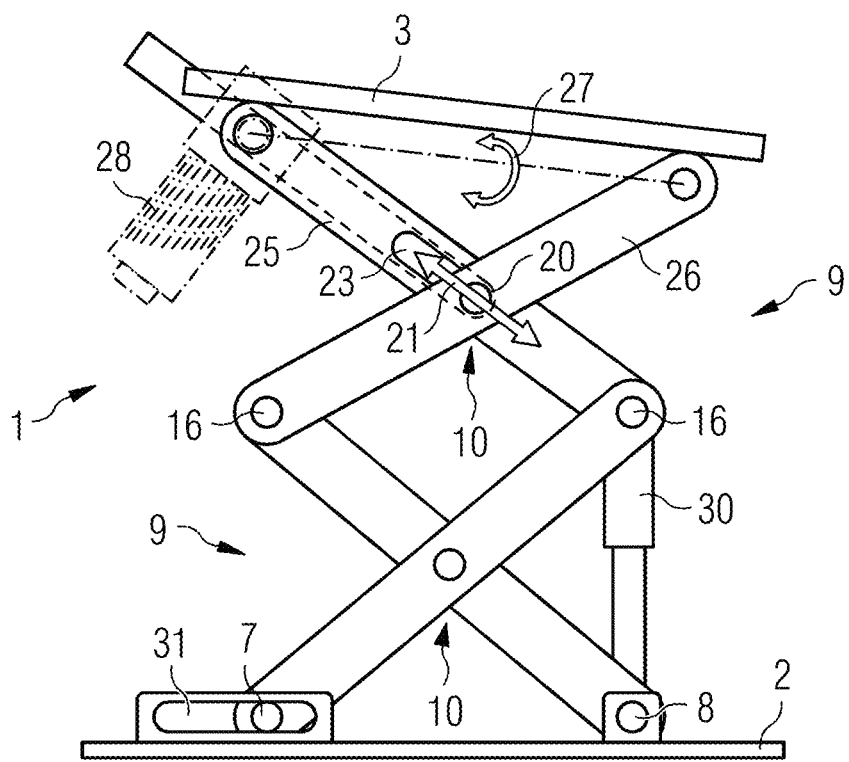
Figure 2C:
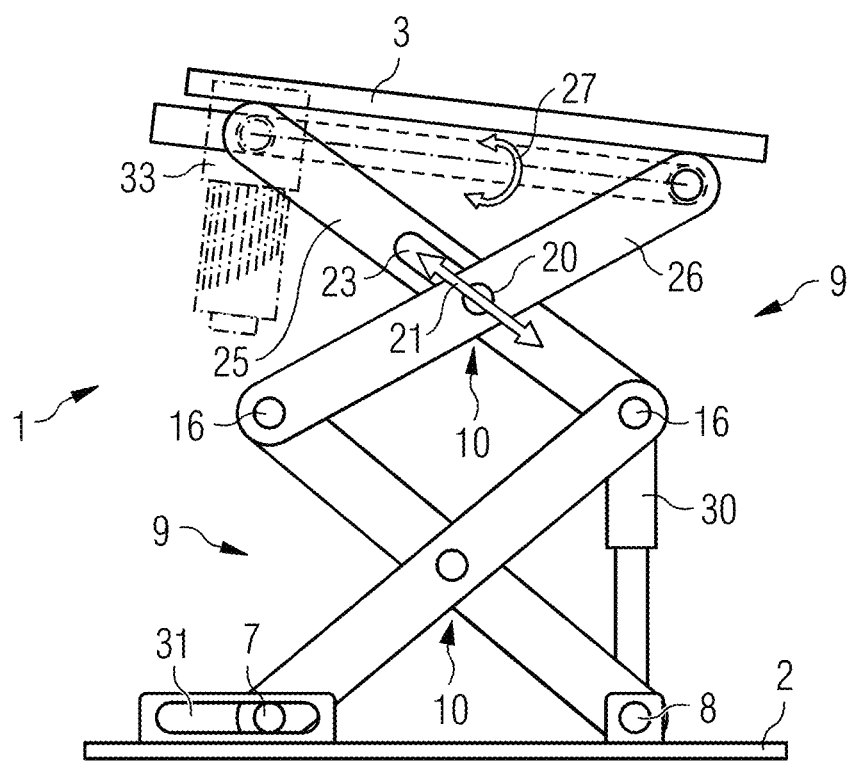

FIGS. 2A-2C show a side view of one embodiment of a patient-supporting apparatus with a lifting apparatus 1 that is arranged between a lower part 2 and an upper part 3. The lifting apparatus 1 may lift the upper part 3 vertically in relation to the lower part 2. The upper part 3 may be configured in the form of a table top or may serve as a holder for a table top.

Figure 1:
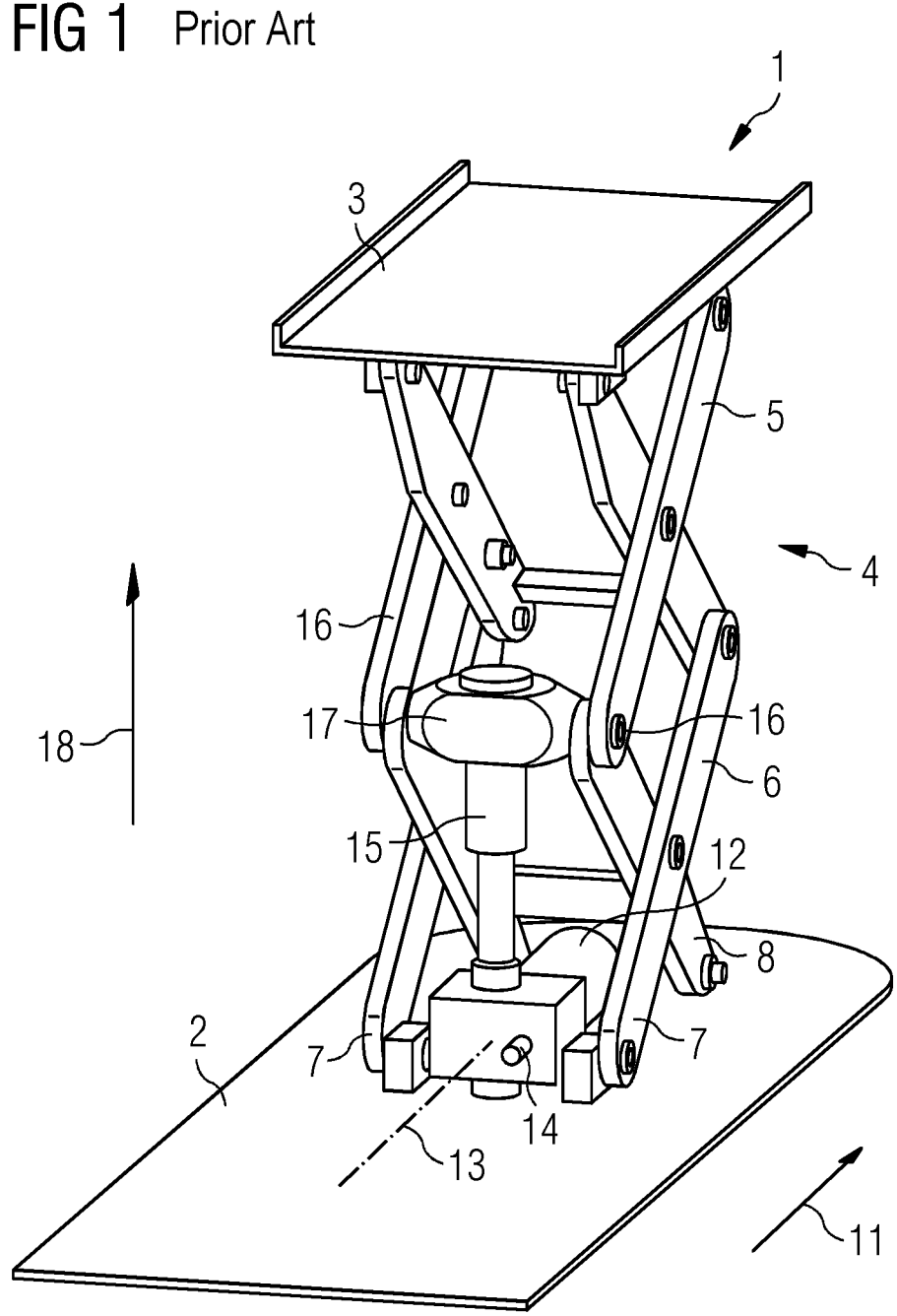
FIG. 1 shows a three-dimensional view of a patient-supporting apparatus according to the prior art.

The lifting apparatus 1 includes a lifting linkage 4 that is formed from two scissors-form sub-linkages 9 arranged one above the other (e.g., upper and lower sub-linkages). The upper and the lower sub-linkages 9 are connected to one another in a movable manner via connecting articulations 16. A third drive unit 30, responsible for the vertical movement of the lifting linkage 4, acts on one of the connecting articulations 16. In one embodiment, as illustrated in FIG. 1, the lifting linkage 4 may be formed from scissors-structure pairs. A rear scissors foot 8 is fixed to the lower part 2. A front scissors foot 7 is arranged such that the front scissors foot 7 may be displaced in a linear guide 31, and this allows the lifting linkage 4 to execute the vertical movement during opening and closing of the sub-linkages 9.

The upper sub-linkage 9 includes a first scissors arm 25 and a second scissors arm 26 that are both connected to one another by a central articulation 10, such that the first scissors arm 25 and the second scissors arm 26 may be rotated about the point of rotation 20. So that the upper part 3 may execute a rotating tilting movement 27 (e.g., a tilting action about a transverse axis), the point of rotation 20 of the central articulation 10 may be displaced in the displacement direction 21 in a slot 23 formed in the first scissors arm 25. The displacement takes place with the aid of a first drive unit 28 (illustration B). The first drive unit 28 may include, for example, a ball screw spindle.

The displacement of the point of rotation 20 causes the upper end of the second scissors arm 26 to be displaced in the vertical direction. The upper end of the first scissors arm 25 maintains a vertical position. This results in the tilting movement 27, which inclines the upper part 3 in relation to a horizontal.

Figure 3A:
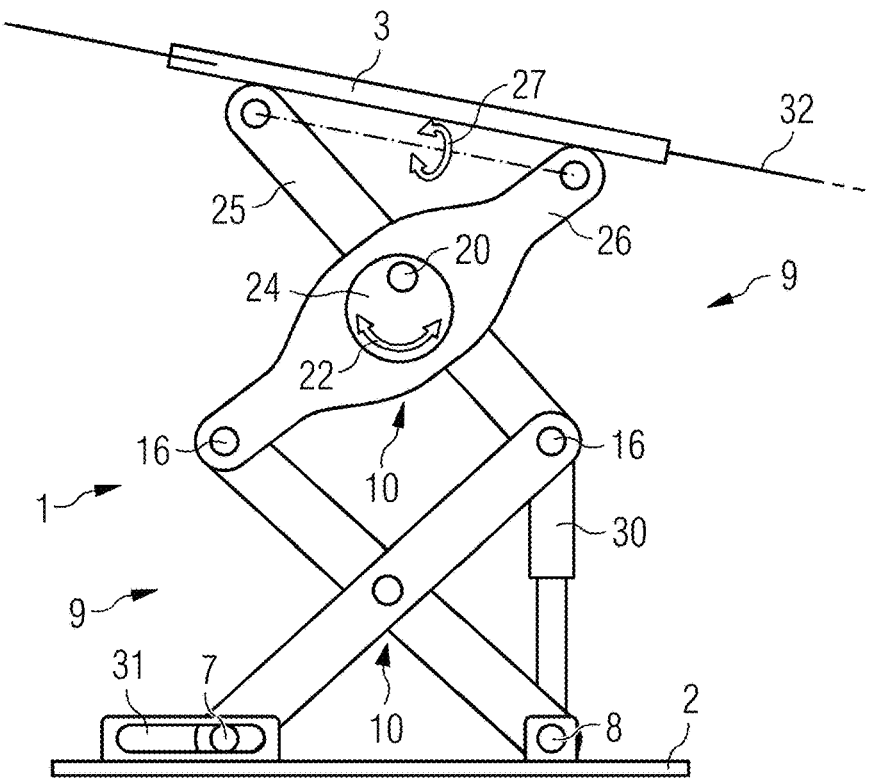
FIGS. 3A and 3B shows two side views of a further embodiment of a tiltable patient-supporting apparatus.
Figure 3B:
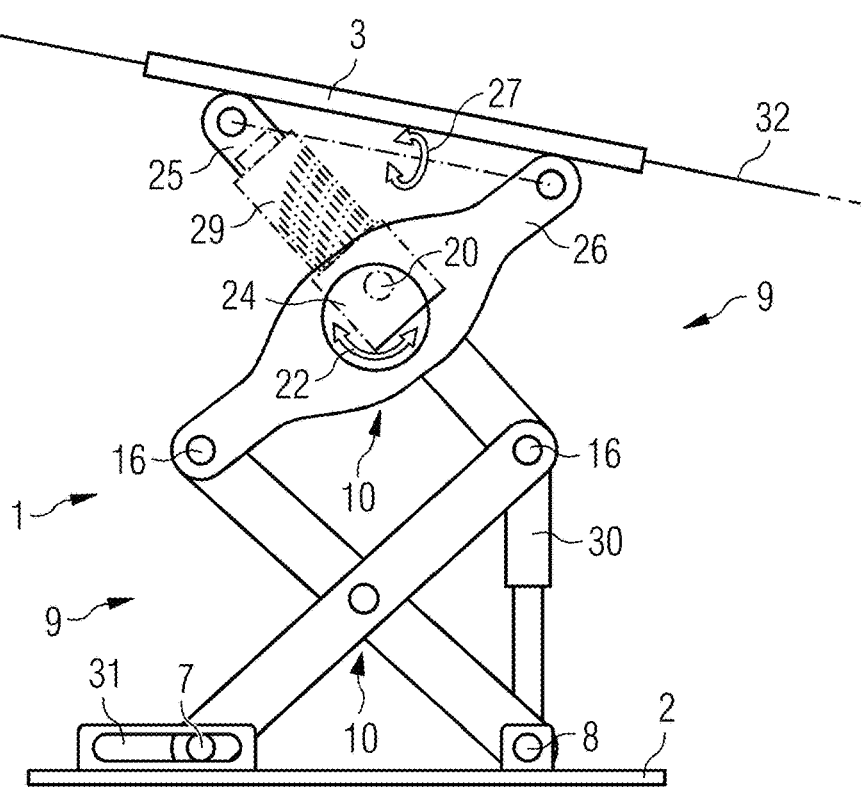

FIGS. 3A and 3B show a side view of another embodiment of a further patient-supporting apparatus with a lifting apparatus 1. The lifting apparatus 1 is arranged between a lower part 2 and an upper part 3 and may lift the upper part 3 vertically in relation to the lower part 2. The upper part 3 serves as a holder for a table top 32, on which a patient may lie.

The lifting apparatus 1 includes a lifting linkage 4 that is formed from two scissors-form sub-linkages 9 arranged one above the other. The upper and the lower sub-linkages 9 are connected to one another via connecting articulations 16. A third drive unit 30, responsible for the vertical movement of the lifting linkage 4, acts on one of the connecting articulations 16. As illustrated in FIG. 1, the lifting linkage may also be formed from scissors-structure pairs. The rear scissors foot 8 is fixed to the lower part 2. The front scissors foot 7 is arranged such that the front scissors foot 7 may be displaced in a linear guide 31, so that the lifting linkage 4 may execute the vertical movement.

The upper sub-linkage 9 includes a first scissors arm 25 and a second scissors arm 26 that are connected to one another by a central articulation 10 such that the first scissors arm 25 and the second scissors arm 26 may be rotated about the point of rotation 20. So that the upper part 3 may execute a rotating tilting movement 27 (e.g., a tilting action about a transverse axis), the central articulation 10 is configured in the form of an eccentric 24. As a result of this, the point of rotation 20 of the central articulation 10 may rotate eccentrically in the direction of rotation 22. The rotation of the eccentric 24 takes place with the aid of a second drive unit 29 (illustration B). The second drive unit 29 may have a worm-gear mechanism (e.g., a worm wheel). The worm wheel is fitted on the eccentric 24.

In mechanics and mechanical engineering, an eccentric 24 is a control disk that is fitted on a shaft and of which a center point is located outside the shaft axis. The eccentric 24 may convert rotary movements into lengthwise movements.

The rotation of the point of rotation 20 causes the upper end of the first scissors arm 25 to be displaced in the vertical (and horizontal) direction, wherein the upper end of the second scissors arm 26 maintains a vertical position. This results in the tilting movement 27, which inclines the upper part 3 in relation to a horizontal.

In the embodiments according to FIGS. 2A-2C and 3A-3B, the configuration also gives rise to the upper part 3 being displaced horizontally when the upper part 3 is tilted. This undesired movement may be compensated for straightforwardly by a horizontal movement in the opposite direction of the patient-supporting apparatus. This is illustrated by way of example in FIG. 2C. The upper part 3 may be displaced with the aid of the fourth drive unit 33.

Depending on the design and tilting angle required, the scissors mechanism according to one or more of the present embodiments may be integrated in just one of the two sub-linkages 9 (as illustrated in FIGS. 2A-2C and 3A-3B) or else in both sub-linkages 9.

The elements and features recited in the appended claims may be combined in different ways to produce new claims that likewise fall within the scope of the present invention. Thus, whereas the dependent claims appended below depend from only a single independent or dependent claim, it is to be understood that these dependent claims may, alternatively, be made to depend in the alternative from any preceding or following claim, whether independent or dependent. Such new combinations are to be understood as forming a part of the present specification.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. A patient-supporting apparatus comprising:
    a lifting apparatus comprising:
        an upper part;
        a lower part;
        a lifting linkage that connects the upper part to the lower part, the lifting linkage comprising at least one scissors-form sub-linkage having a first central articulation;
        an upper drive unit directly connected to the first central articulation of the at least one scissors-form sub-linkage; and
        a horizontal drive unit connected to the upper part, the horizontal drive unit being configured to act on the upper part to displace the upper part in a direction along a longitudinal axis of the upper part when the upper part is tilted to compensate for the tilting of the upper part,
    wherein a point of rotation of the first central articulation is arranged in a displaceable manner such that the upper part is tiltable in a transverse direction of the upper part,
    wherein the upper drive unit acts on the first central articulation to displace the point of rotation.

2. The patient-supporting apparatus of claim 1, wherein the upper part is configured in the form of a table top.

3. The patient-supporting apparatus of claim 1, further comprising a table top that is arranged on the upper part.

4. The patient-supporting apparatus of claim 1, wherein the at least one scissors-form sub-linkage comprises two sub-linkages that are arranged one above the other and are connected to connecting articulations so as to form a double scissors structure,
    wherein the first central articulation is formed in an upper sub-linkage of the two sub-linkages.

5. The patient-supporting apparatus of claim 1, wherein the at least one scissors-form sub-linkage comprises two sub-linkages that are arranged one above the other and are connected to connecting articulations so as to form a double scissors structure,
    wherein the first central articulation is formed in an upper sub-linkage of the two sub-linkages and a second central articulation is formed in a lower sub-linkage of the two sub-linkages.

6. The patient-supporting apparatus of claim 1, further comprising a first scissors arm and a second scissors arm that form the sub-linkage and are connected to one another by the first central articulation such that the first scissors arm and the second scissors arm are rotatable about the point of rotation,
    wherein the first central articulation is configured in the form of an eccentric, to rotate the point of rotation eccentrically.

7. The patient-supporting apparatus of claim 6, wherein the upper drive unit is configured to rotate the eccentric.

8. The patient-supporting apparatus of claim 4, further comprising a lower drive unit configured to adjust the upper part in height,
    wherein the lower drive unit acts on one of the connecting articulations.

9. The patient-supporting apparatus of claim 8, wherein the lower drive unit is configured for a rectilinear movement of the upper part in the vertical direction.

10. A method of tilting a patient-supporting apparatus, the patient-supporting apparatus comprising a lifting apparatus comprising an upper part, a lower part, a lifting linkage that connects the upper part to the lower part, the lifting linkage comprising at least one scissors-form sub-linkage having a central articulation, a drive unit directly connected to the central articulation of the at least one scissors-form sub-linkage, wherein a point of rotation of the central articulation is arranged in a displaceable manner such that the upper part is tiltable in a transverse direction of the upper part, wherein the drive unit acts on the central articulation to displace the point of rotation, and a horizontal drive unit connected to the upper part, the horizontal drive unit being configured to act on the upper part to displace the upper part in a direction along a longitudinal axis of the upper part when the upper part is tilted, the method comprising:
    moving the point of rotation of the central articulation such that the upper part is tilted in the transverse direction.

11. A patient-supporting apparatus comprising:
    a lifting apparatus comprising:
        an upper part;
        a lower part;
        a lifting linkage that connects the upper part to the lower part, the lifting linkage comprising an upper sub-linkage configured to tilt the upper part in a transverse direction of the upper part and a lower sub-linkage configured to adjust the upper part in height, the upper sub-linkage being arranged above the lower sub-linkage, wherein the upper sub-linkage and lower sub-linkage are connected to connecting articulations so as to form a double scissors structure;
        a lower drive unit connected to the lower sub-linkage, the lower drive unit configured to adjust the lower sub-linkage in height, such that the upper part is moveable in a vertical direction; and
        an upper drive unit directly connected to a central articulation of the upper sub-linkage,
    wherein a point of rotation of the central articulation of the upper sub-linkage is arranged in a displaceable manner such that the upper part is tiltable in a transverse direction of the upper part, the central articulation being configured in the form of an eccentric to rotate the point of rotation eccentrically,
    wherein the upper drive unit acts on the central articulation and is configured to rotate the eccentric.

* * * * *